United States Patent [19]

McCormick

[11] Patent Number: 4,917,930

[45] Date of Patent: Apr. 17, 1990

[54] PERFLUORO COMPOUND DISPERSIONS CONTAINING REDUCED AMOUNTS OF SURFACTANT AND PROCESS OF PREPARATION

[75] Inventor: William McCormick, Carlisle, Mass.

[73] Assignee: Adamantech, Inc., Linwood, Pa.

[21] Appl. No.: 914,961

[22] Filed: Oct. 3, 1986

Related U.S. Application Data

[63] Continuation-in-part of Ser. No. 794,271, Nov. 4, 1985, abandoned, which is a continuation of Ser. No. 600,653, Apr. 16, 1984, abandoned.

[51] Int. Cl.$^4$ .................. A61K 31/74; A61K 31/025
[52] U.S. Cl. ...................................... 424/78; 514/755; 514/756; 514/832
[58] Field of Search ................. 424/78; 514/755, 756, 514/832

[56] References Cited

U.S. PATENT DOCUMENTS

| | | | |
|---|---|---|---|
| 3,547,995 | 12/1970 | Bartlett | 564/201 |
| 3,778,381 | 12/1973 | Rosano et al. | 424/342 |
| 3,828,085 | 8/1974 | Price et al. | 424/320 |
| 3,911,138 | 10/1975 | Clark | 424/352 |
| 3,993,581 | 11/1976 | Yokoyama et al. | 424/352 |
| 4,105,798 | 8/1978 | Moore et al. | 435/1 |
| 4,443,480 | 4/1984 | Clark | 424/352 |
| 4,461,717 | 7/1984 | Moore | 424/352 |

OTHER PUBLICATIONS

Clark, Biomedical Aspects of Fluorine Chem., ed. Fuller et al.; Elsevier Biomedical Press, 1982.
Yokoyama et al., Biochemical Aspects of Fluorine Chemistry, ed. Fuller et al.; Elsevier Press, 1982.

*Primary Examiner*—Leonard Schenkman
*Attorney, Agent, or Firm*—J. Edward Hess; Donald R. Johnson

[57] ABSTRACT

Compositions having enhanced gas and drug transporting capability, are prepared by providing a perfluoro compound dispersed in an aqueous medium with a surfactant to form an aqueous initial dispersion, concentrating the perfluoro compound phase of the dispersion as by centrifugation or filtration, wherein a portion of the surfactant remains complexed with the particles of the perfluoro compound phase and the balance of the surfactant is in the aqueous phase, separating the phases, and redispersing the particles of the concentrated perfluoro compound phase to form a final dispersion in which greater than 65% by weight, and preferably at least 75%, of the surfactant present is complexed with the perfluoro compound particles.

20 Claims, No Drawings

PERFLUORO COMPOUND DISPERSIONS CONTAINING REDUCED AMOUNTS OF SURFACTANT AND PROCESS OF PREPARATION

RELATED APPLICATION

This application is a continuation in-part of U.S. Ser. No. 794,271, filed Nov. 4, 1985, abd. which in turn is a continuation of U.S. Ser. No. 600,653, filed Apr. 16, 1984, now abandoned. This application is also related to U.S. application Ser. No. 313,124 filed Oct. 20, 1981 by Robert E. Moore and entitled "Preparation of a Gel Having Gas Transporting Capability", (now U.S. Pat. No. 4,569,784).

BACKGROUND OF THE INVENTION

This invention relates to aqueous dispersions of perfluoro compounds useful as gas transfer agents and for drug delivery and other therapeutic applications in animals including man. Typical perfluoro compounds, dispersions and uses are described in U.S. Pat. Nos. 3,911,138 to Clark and 4,105,798 to Moore and Clark. The perfluoro compounds described in these patents are essentially non-toxic and therefore eminently suitable for therapeutic uses.

Aqueous dispersions of perfluoro compounds, such as those of the U.S. patents cited above, are prepared by dissolving a surfactant in water, adding the perfluoro compound, and then agitating the mixture until a uniform dispersion of the perfluoro compound is obtained. Since the perfluoro compounds are extremely hydrophobic, considerable mechanical energy is required for effective dispersion, such as high pressure homogenization or sonically induced cavitation. Depending on selection of perfluoro compound, surfactant and proportions of ingredients, highly stable dispersions of very small average particle size, on the order of about 0.1 to 1.0 micron in diameter, are obtained. In such cases, the dispersions are essentially transparent and are sometimes described in the literature as "microemulsions" (U.S. Pat. No. 3,778,381 to Rosano et al). However, in other cases useful dispersions can be prepared having larger average particle sizes and these may be borderline between suspensions and emulsions. Accordingly, the term "dispersion" is used in this specification to indicate, generically, any two-phase system, whether a suspension, emulsion or microemulsion, and whether oil-in-water, water-in-oil or invert, and the term "perfluoro compound phase" means the perfluoro compound-containing particles of the dispersion. For purposes of illustration, the emphasis in this specification will be on the more preferred compositions, viz., emulsions or microemulsions of the oil-in-water type.

To overcome the difficulty of forming good dispersions with the extremely hydrophobic perfluoro compounds it is common practice to prepare the dispersions using a high proportion of surfactant to perfluoro compound (of the order of about 1:5 by weight) and low concentrations of perfluoro compound (about 20-25% w/v). This facilitates not only good dispersability but also small particle size. The resulting dispersions have good stability and low viscosity which promote their rapid transit throughout the cardiovascular system, particularly in capillaries or vessels which are blocked or constricted. Such dispersions will also exhibit reduced retention in the reticuloendothelial system (RES). However, the goal of optimizing the dispersion process and physical qualities of the dispersion (particularly stability and viscosity) imposes a practical upper limit on the amount of perfluoro compound in the finished dispersions and thereby also limits the gas transfer capacity of the dispersions and their capacity for treatment of hypoxic cells and for carrying lipophilic drugs in the manner described in copending, commonly assigned U.S. application Ser. No. 580,760 filed Feb. 17, 1984. The subject matter of said application and its predecessor applications is incorporated herein by reference.

Additionally, while it is possible (although not always practical because of formulation difficulties) to select surfactants and/or dosages thereof which are sufficiently non-toxic by $LD_{50}$ standards, other toxic responses attributable to the surfactants, such as complement activation, have been reported. This has led either to excluding the surfactants from use in perfluoro compound dispersions or to reduction in their concentration with proportionate reduction in the amount of perfluoro compound which can be effectively dispersed.

In summary, it has heretofore been considered necessary, in order to satisfy the requirements of efficient dispersability, low particle size, stability and viscosity on the one hand, and sufficient gas transfer capacity and biological compatibility on the other, to maintain fairly low concentrations of perfluoro compound in aqueous dispersions thereof, on the order of no more than about 25% (w/v), i.e., about 25 g/100 ml. of the total dispersion, so that the amount of surfactant may also be kept low, on the order of no more than about $2 \geqq 5\%$ (w/v), i.e., about 2-5 g/100 ml. of the total dispersion.

SUMMARY OF THE INVENTION

It has now been found, in accordance with the invention, that the amount of surfactant heretofore regarded as necessary in forming high quality, biologically compatible, therapeutic aqueous dispersions of perfluoro compounds, can be substantially and even drastically reduced without diminishing ability to maintain the perfluoro compounds in stable, uniform dispersion and without sacrificing those properties of the dispersions which contribute to therapeutic efficacy, such as low viscosity, stability and high amounts of perfluoro compound. Quite the contrary, the perfluoro compound dispersions can now be even more efficiently prepared and can contain higher amounts of the perfluoro compound than heretofore deemed possible, but with the low particle size, low viscosity and good stability which are the hallmarks of the earlier dispersions described in the Clark and Moore patents cited above.

These seemingly contradictory, but highly beneficial results are obtained (in one method of practice of the invention) by (a) providing an initial aqueous dispersion of perfluoro compound and surfactant, (b) concentrating the perfluoro compound phase of the initial dispersion, (c) separating all or part of the concentrated perfluoro compound phase from the aqueous phase, and (d) redispersing the concentrated perfluoro compound phase in an aqueous medium. "Concentrating" as the term is used herein, means condensing, amassing or gathering together the perfluoro compound particles to form a perfluoro compound phase more concentrated in perfluoro compound than in the initial dispersion. The redispersion may be achieved with sterile water alone or redispersion may be facilitated by addition of an aqueous medium containing suitable additional surfactant or other agent. Moreover, as hereinafter described, the foregoing concentration, separation and redispersion steps may be practiced in a continuous manner and/or may be combined with classification of the concentrated perfluoro compound phase particles with consequent even greater uniformity of particle size.

In one aspect of the invention, therefore, there is provided a method of preparing aqueous dispersions of perfluoro compounds having the advantage of reduction, in the final dispersion, of the amount of surfactant heretofore considered necessary for such dispersions.

In another aspect of the invention, the aforesaid method additionally affords the opportunity to use, in preparing the initial dispersion, the higher proportions of surfactant to perfluoro compound known to facilitate more efficient dispersion and the formation of high quality dispersions of perfluoro compounds but without, ultimately, increasing the viscosity to undesirable levels or introducing the unacceptable toxicity associated with many surfactants. For internal use the dispersions of the invention will have viscosities at body temperature (37° C.) of no greater than the viscosity of blood and preferably considerably lower, e.g., from about the viscosity of water (about 0.7 centipoise) to about 3.0 centipoise.

In still another aspect of the invention, aqueous dispersions of perfluoro compounds are provided which contain higher amounts of perfluoro compound and lower amounts of surfactant than have heretofore been deemed capable of providing satisfactory dispersions, with proportionately improved capacity for gas transfer and therapeutic effect, and proportionately diminished toxicity attributable to the surfactant.

In a further, highly significant and preferred aspect of the invention, aqueous dispersions of perfluoro compounds are provided which not only have the characteristics described in the foregoing aspects, but also have controlled, small particle size range, low viscosity and good stability. These improvements lead to desirable biological characteristics such as good cardiovascular residence time and low RES retention, and ultimately to greater therapeutic benefit of the nature described in the aforementioned Clark and Moore patents and U.S. application Ser. No. 580,760.

DETAILED DESCRIPTION

The extraordinary benefits of the invention are based in part upon the discovery that when the perfluoro compound phase of the initial dispersion is concentrated, a portion, often a minor portion, of the surfactant will remain with the perfluoro compound particles and the balance of the surfactant, often a high percentage, will be in the aqueous phase. The concentrated perfluoro compound phase is then separated from the aqueous phase and readily redisperses in an aqueous medium, thereby leaving behind the surfactant removed with the aqueous phase in the separation step. The redispersed perfluoro compound phase thus comprises an emulsion in which a very high percentage of the surfactant present in this final dispersion, i.e. greater than about 65% by weight, preferably at least 75% by weight, and most preferably at least about 85–90%, up to an almost theoretical 100% of the surfactant present, is complexed with the perfluoro compound. This is to be contrasted with prior art emulsions such as those described in U.S. Pat. No. 4,105,798, wherein when perfluoro-adamantanes such as dimethyladamantane are emulsified with surfactants such as polyoxyethylene-polyoxypropylene copolymers (e.g. "Pluronic F-68"), the percentage of surfactant present which is complexed with the perfluoro compound is significantly lower. Similarly, when dimethyladamantane is emulsified with a perfluoro-amidoamine oxide surfactant, as taught in U.S. Pat. No. 4,461,717, the amount of surfactant present complexed with the perfluoro compound averages about 55% by weight. (See Example 14.) Thus, in order to obtain emulsions containing the high percentages of complexed surfactant of this invention, it is necessary that the amount of free surfactant such as are present in the prior art emulsions be reduced substantially, as taught herein.

In some cases the concentration step results in two distinct layers comprising a perfluoro compound phase and an aqueous phase. When practiced continuously, as described below, layering of the phases usually will not be observed due to the dynamic characteristics of the process but concentrating, separation and redispersion nevertheless occur.

It is not fully understood how or why this phenomenon occurs. In some manner a portion of the surfactant binds with or is adsorbed to the perfluoro compound, thus forming perfluoro compound-containing particles during the initial dispersion process and/or the concentrating step in which surfactant is so tightly bound that it remains "complexed" with the perfluoro compound particles during the subsequent concentrating and/or phase separation steps. The other portion of the surfactant remains free (uncomplexed) in the continuous, aqueous phase of the initial dispersion. Thus, an important finding of the invention is that a portion, and often a substantial portion of the surfactant present in the initial dispersion remains as free, uncomplexed surfactant and therefore is separated from the perfluoro compound phase. Accordingly, the free surfactant is not carried through to the final dispersion. The balance of the surfactant remains associated with the perfluoro compound-containing particles in sufficient amounts to permit the redispersion.

Consequently, according to the invention, larger amounts of surfactant (and higher proportion of surfactant to perfluoro compound) known to facilitate the initial dispersion can now be used but without their ultimate adverse effects, namely, unacceptable viscosity and/or toxicity of the final dispersion due to such larger amounts of surfactant.

Significantly, also, the larger amounts of surfactant now permissible in the initial dispersion also permit larger amounts of perfluoro compound, e.g., greater than the 20–25% (w/v) heretofore considered the practical upper limit, and therefore provide higher gas transfer capacity than is possible with dispersions containing smaller amounts of perfluoro compound, while permitting suitably small particle size and low viscosity.

For the purposes of this specification, the surfactant remaining with the perfluoro compound particles during the concentration and separation steps is identified as "associated" surfactant, and the surfactant remaining in the separated aqueous liquid is called "free" surfactant. Surfactant employed in forming the initial dispersion (prior to concentrating and separating) is sometimes called "principal" surfactant herein to distinguish it from any additional ("auxiliary") surfactant which optionally may be used for the redispersion step. Where "surfactant" is referred to without qualification, surfactant employed in forming the initial dispersion is understood. The terms "initial dispersion" and "final dispersion" are used herein to mean, respectively, the dispersion provided in the first step of the process of the invention and the dispersion resulting from the subsequent steps of the process.

The amount of associated surfactant in the concentrated perfluoro compound phase which is "complexed" with the perfluoro compound, can be determined by taking a sample of the redispersed emulsion, concentrating the perfluoro compound phase of the sample, measuring the amount of the surfactant in the resulting supernatant layer, and subtracting this amount from the known total amount of surfactant in the sample, which total amount can be calculated as shown below, thus giving the amount of surfactant "complexed" within the particles of the concentrated perfluoro compound phase. The process has been practiced successfully, and the novel composition of this invention obtained, if the calculated difference, i.e. the amount of complexed surfactant, is greater than the amount of surfactant in the supernatant layer, to the extent of greater than about 65% by weight of the total surfactant present, and preferably at least 75% by weight. In some cases, depending upon the extent to which the surfactant "complexes" with the perfluorocarbon, this may show that most of the surfactant was removed during the phase concentration and separation steps practiced on the initial dispersion when forming the final dispersion. In any event, it should indicate that a high proportion of the associated surfactant in the concentrated perfluoro compound phase is "complexed" with the perfluoro compound in the final dispersion and only a very small, even minute, amount is found in the aqueous phase. As stated above, greater than about 65% by weight of the surfactant present in the final dispersion should be complexed with the perfluoro compound, and preferably at least 75%. "Complexed" surfactant, as the term is used herein, denotes surfactant which remains with the concentrated perfluoro compound phase material after removal of the aqueous phase. While it is believed that such surfactant does not chemically combine with the perfluoro compound phase material, the invention is not to be limited by any theory as to the nature of the association, whether physical, chemical or a combination thereof.

The total amount of surfactant present in a redispersed emulsion can be measured by either of two methods, i.e. by heating the emulsion until the perfluorocarbon and water are driven off, or by freeze drying the emulsion and removing the perfluorocarbon and water by vacuum drying. The residue, in each case, is the surfactant, which can then be measured by gravimetric analysis. When the amount of surfactant in the supernatant, as measured above, is then subtracted from the total amount in the emulsion, the remainder will then represent the surfactant which was complexed with the perfluorocarbon.

In determining the amount of complexed surfactant in an aqueous dispersion of a perfluoro compound, centrifigation conditions are used which result in separation of the dispersion into a supernatant aqueous layer and a lower layer which is still a perfluorocarbon dispersion, the integrity of the dispersion having been retained, but which is more concentrated with respect to perfluoro compound as a result of the removal of water therefrom into the aqueous layer. When the dispersion of the invention is centrifuged under the conditions set forth in Runs 4 through 9 in Table I below, a major proportion of the surfactant remains complexed in the perfluoro compound phase. In some embodiments when the dispersion is centrifuged under the stronger conditions, for example as set forth in Run 10 in Table I, below, a very high proportion of the surfactant remains complexed with the perfluoro compound phase.

In a further embodiment of the invention, it has been found to be highly desirable, especially when the emulsion is for systemic administration, to concentrate, recover, and redispersed the perfluoro compound phase a second time following the first redispersion, in order to remove any remaining occluded or otherwise nonbound surfactant from the perfluoro compound. In that case, the first redispersion can be considered a washing step. A second redispersion, if desired, is generally sufficient since additional redispersions (or washings) may result in breaking the emulsion where the binding of the surfactant and perfluoro compound is not a stable one. Certain types of surfactants, in fact, start to break up after one dispersion (washing). Indeed, for purposes of determining the stability of an emulsion, the number of washings which an emulsion can undergo without breaking up can be used as a test of the particle, and thus emulsion, stability.

As described above, a measurement of a suitable sample of each redispersion to determine the amount of surfactant in the supernatant serves as an indication of the amount of surfactant which remains bound to the perfluoro compound. That is, by measuring the total amount of surfactant in the redispersion and subtracting the amount in the supernatant, the bound quantity is readily determined. In each redispersion, if the surfactant-perfluoro compound "complex" is a stable one, then as the amount of surfactant in the supernatant decreases as a result of this process, the percentage of surfactant bound to the perfluoro compound, relative to the amount in the supernatant, remains constant or slightly increases to provide the emulsified composition of this invention in which a very high percentage of the surfactant is bound to the perfluoro compound.

DISPERSIONS OF THE INVENTION

The perfluoro compounds used in preparing the dispersions of the invention are any fluorinated hydrocarbons or hetero-atom containing derivatives thereof which exhibit gas transfer properties, and which are capable of dispersion in an aqueous medium and of systemic administration as aqueous dispersions to animals including man. The compounds may be substantially fluorinated or completely fluorinated and are generally, but not necessarily, liquids at ambient temperature and pressure.

"Substantially fluorinated" in this specification means that most of the hydrogen atoms of a compound have been replaced by fluorine atoms, such that further replacement does not substantially increase the gas transport capability of the material. It is believed that this level is reached when at least about 80-90% of the hydrogen atoms have been replaced by fluorine atoms. However, it is preferred that at least 95% of the hydrogen atoms have been replaced, more preferably at least 98% and even more preferably, 100%. In the aforementioned U.S. Pat. Nos. 3,911,138 and 4,105,798, the ability to transport oxygen is related to the solubility in the materials of a gas such as oxygen. These patents suggest that the perfluorinated materials will absorb 10-100 cc of oxygen per 100 cc of material at 25° C. and 760 milliliters of mercury.

Among the fluorinated materials suitable for use in this invention include those which are broadly described as cyclic perfluorohydrocarbons or derivatives thereof.

Examples are the perfluorinated derivatives of chemically inert, non-aromatizable $C_9$–$C_{18}$ polycyclic compounds such as bicyclononanes (e.g., bicyclo [3.3.1] nonane, 2,6-dimethylbicyclo [3.3.1] nonane, 3-methylbicyclo [3.3.1] nonane and trimethylbicyclo [3.3.1] nonane); adamantane and alkyl ($C_1$–$C_6$) adamantanes such as methyl and dimethyladamantane, ethyl and diethyladamantane, trimethyladamantane, ethylmethyladamantane, ethyldimethyladamantane and triethyladamantane; methyldiadamantane and trimethyldiadamantane; methyl and dimethylbicyclooctanes; tetrahydrobinor-S, pinane, camphane, decalin and alkyl decalins such as 1-methyldecalin; and 1,4,6,9-dimethanodecalin; bicyclo [4.3.2] undecane, bicyclo [5.3.0] decane, bicyclo [2.2.1] octane, tricyclo [5.2.1.0$^{2,6}$] decane, methyltricyclo [5.2.1.0$^{2,6}$] decane, and the like; or any mixtures thereof.

Hetero atom-containing perfluoro compounds include F-tributyl amine, F-tripropyl amine and F-N,N-dimethylcyclohexylmethylamine; perfluoro ethers such as F-2-butyltetrahydrofuran, F-2-butylfuran, F-hydrofuran, the 1,2,2,2-tetrafluoromethyl ether of F-(2,5,8-trimethyl-3,6,9-trioxa-1-dodecanol), and other hetero compounds such as F-N-methyldecahydroquinoline, F-1-methyloctahydroquinolizine, F-octahydroquinolidine and F-N-cyclohexylpyrrolidine.

Aromatic and aliphatic compounds include F-naphthalene, F-1-methyl-napthalene, F-n-ethyl-morpholine, F-n-heptane, F-dodecane and 1,2-bis-nonylfluorobutylethylene. Monocyclic aliphatic compounds include F-trimethylcyclohexane, F-isopropylcyclohexane, F-tetramethylcyclohexane, F-n-butylcyclohexane, F-1-methyl-4-isopropylcyclohexane, F-p-diisopropylcyclohexane and similar compounds.

Certain of the fluorine atoms of the foregoing materials may be substituted by other halogen atoms such as bromine. Included among these compounds, are, for example, monobrominated compounds such as 1-bromo-pentadecafluoro-4-isopropylcyclohexane, 1-bromotridecafluorohexane, 1-bromo-pentadecafluorooctane, 1-bromo-pentadecafluoro-3-isopropylcyclopentane and perfluoro-1-bromobutylisopropyl ether, or polybrominated derivatives thereof.

Perfluorinated $C_8$ or lower materials and up to $C_{18}$ or higher materials, included partially brominated analogs thereof, as well as mixtures of various different perfluoro compounds can be used in this invention.

Those of the foregoing fluorinated compounds which are solid at ambient temperature can be dissolved in a suitable solvent or in other perfluorocompounds which are liquid at ambient temperatures, and the resulting mixture can be used to form the dispersions of the invention. "Liquid" in this specification when describing the fluoro compounds therefore means either a fluoro compound which is per se liquid at ambient temperatures or a solution of a solid fluoro compound in a fluoro compound solvent.

The more preferred perfluoro compounds for use in the invention on the basis of relative inertness (chemical and biological), good dispersability and residence time are the perfluoro $C_9$–$C_{18}$ polycyclic hydrocarbons of U.S. Pat. No. 4,105,798, and particularly F-dimethyladamantane, F-trimethylbicyclo [3.3.1] nonane, F-tricyclo [5.2.1.0$^{2,6}$] decane, F-methyltricyclo [5.2.1.0$^{2,6}$] decane, F-bicyclo [5.2.0] decane and F-methylbicyclo [5.2.0] decane, including any isomers thereof, and mixtures of such compounds, for example mixtures of F-dimethyladamantane and F-trimethylbicyclo [3.3.1] nonane, ranging from about 90/10 to 10/90 by weight.

The preferred dispersants for uniformly dispersing the perfluoro compounds in an aqueous medium are the nonionic, i.e. uncharged, surfactants. In some compositions and systems of the invention, particularly those cases where the dispersions are used non-systemically, such as in topical or local treatments, ionic or amphoteric surfactants may be used to disperse the perfluoro compounds. Because systemic treatments require careful attention to physiological acceptability of the compounds, such as isotonic character, ionic surfactants are less desirable, although it is possible to offset or moderate their ionic character by formulating the dispersions with electrolytes or other additives.

Suitable nonionic surfactants include aliphatic materials such as oxyethylene or oxypropylene homopolymers or block copolymers of ethylene oxide and propylene oxide comprising a hydrophobic propylene oxide section combined with one or more hydrophilic ethylene oxide sections, for example the "Pluronic" (trademark) surfactants available from BASF-Wyandotte, Inc. Less desirably, aromatic types may also be used, such as alkylphenoxypolyethoxyethanols having alkyl groups of about 7 to 18 carbon atoms and 1 to 60 or more oxyethylene units, for example: heptylphenoxypolyethoxyethanols, octylphenoxypolyethoxyethanols, methyloctylphenoxypolyethoxyethanols, nonylphenoxypolyethoxyethanols, dodecylphenoxypolyethoxyethanols, and the like; polyethoxyethanol derivatives of methylene linked alkylphenols; sulfur-containing analogs of the foregoing; ethylene oxide derivatives of long-chain carboxylic acids, such as lauric, myristic, palmitic, oleic, and the like or mixtures of acids such as are found in tall oil containing 1 to 60 oxyethylene units per molecule; and analogous ethylene oxide condensates of long-chain or branched-chain amines, such as dodecylamine, hexadecylamine, and octadecylamine, containing 1 to 60 oxyethylene groups.

Naturally occurring emulsifiers or derivatives thereof are also useful. These include the alginates, cellulose derivatives such as methyl cellulose and carboxymethyl cellulose, water soluble gums such as gum arabic and gum tragacanth, the phospholipids (such as lecithin and yolk phospholipid as described in U.S. Pat. No. 4,397,870-Sloviter), and the sterols.

Nonionic fluorine containing surfactants are particularly preferred. The fluorinated alkyl esters are one class of these surfactants, and are commercially available from 3M Company under the designations FC-93, FC-95, FC-128, FC-143, FC-430 and FC-431.

The more preferred nonionic, fluorine containing surfactants, from the standpoint of their exceptional ability to form dispersions which maintain a range of small particle size over substantial periods of time, of the order of 35 weeks to a year or more, even at room temperature, are the fluorinated amidoamine oxides described in U.S. Pat. Nos. 3,828,085 to Price et al, and 3,547,995 to Bartlett. These compounds may be generically described by the formula (1):

(1)

wherein $R_f$ is a perfluoroalkyl radical of 1 to about 25 carbon atoms or a polyfluoroalkoxyalkyl radical wherein the alkoxy group may contain 3 to about 40 carbon atoms of which at least a major portion thereof are perfluorinated and the alkyl group may contain 2 to about 40 carbon atoms, fluorinated or unfluorinated; Y is hydrogen or alkyl of 1 to 6 carbon atoms; R is an alkylene radical of the formula:

$$-C_zH_{2z}$$

wherein z is an integer of 1 to 6; and Q is an aliphatic amine oxide radical of the formula:

$$\begin{array}{c} R_5 \\ | \\ -N-R_6 \\ | \\ O \end{array}$$

wherein $R_5$ and $R_6$ are each alkyl radicals of 1 to 6 carbon atoms or hydroxy-terminated alkyl radicals of 2 to 6 carbon atoms. In all cases the alkoxy, alkyl and alkylene groups may be straight or branched chain.

Preferred subclasses of the surfactants of the foregoing patents are those of the following formulas (2) and (3):

$$C_nF_{2n+1}O(CF_2)_x\overset{O}{\overset{\|}{C}}NH(CH_2)_y\overset{O}{\overset{\uparrow}{N}}R^1R^2 \quad (2)$$

wherein n is at least 3 (preferably 3–10), x is at least 2 (preferably 2–6), y is at least 1 (preferably 2–6), and $R^1$ and $R^2$ independently are alkyl radicals containing 1–6 carbon atoms; and $$C_nF_{2n+1}\overset{O}{\overset{\|}{C}}NH(CH_2)_z\overset{O}{\overset{\uparrow}{N}}R^1R^2 \quad (3)$$

wherein n is at least 3 (preferably 3–10), z is at least 1 (preferably 2–6), and $R^1$ and $R^2$ independently are alkyl radicals containing 1–6 carbon atoms.

Specific amidoamine oxides within the scope of formula (1) are described in Examples 1–6 of U.S. Pat. No. 3,828,085, namely:

$$CF_3(CF_2)_6\overset{O}{\overset{\|}{C}}NH(CH_2)_3\overset{O}{\overset{\uparrow}{N}}(CH_3)_2$$

$$(CF_3)_2CFO(CH_2)_3\overset{O}{\overset{\|}{C}}NH(CH_2)_3\overset{O}{\overset{\uparrow}{N}}(CH_3)_2$$

$$(CF_3)_2CFO(CF_2)_5\overset{O}{\overset{\|}{C}}NH(CH_2)_3\overset{O}{\overset{\uparrow}{N}}(CH_3)_2$$

$$(CF_3)_2CFO(CF_2)_7\overset{O}{\overset{\|}{C}}NH(CH_2)_3\overset{O}{\overset{\uparrow}{N}}(CH_3)_2$$

$$(CF_3)_2CFO(CF_2)_5\overset{O}{\overset{\|}{C}}NH(CH_2)_3\overset{O}{\overset{\uparrow}{N}}(C_2H_5)_2$$

-continued $$(CF_3)_2CFO(CF_2)_8(CH_2)_{10}\overset{O}{\overset{\|}{C}}NH(CH_2)_3\overset{O}{\overset{\uparrow}{N}}(C_2H_5)_2$$

In selecting which dispersant to use, it is well known that these materials may vary widely with respect to their solubility in water and/or in the desired perfluoro compounds. Thus, for example, such water-soluble materials as block copolymers of ethylene oxide or propylene oxide (e.g. "Pluronic F-68") are not very lipophilic, and only relatively small percentages of the dispersant employed in the initial dispersion can be expected to complex with the perfluoro compound, whereas such materials as perfluorinated surfactants, lecithin, and the like are much more lipophilic, and proportionately larger amounts of the initial concentrations of these surfactants will complex with the perfluoro compound. Thus, one skilled in the art can, in light of these known considerations, readily determine those materials and conditions which will provide the desired concentrations of dispersant and perfluoro compounds in the final dispersion.

PREPARATION OF THE DISPERSIONS

To provide the initial dispersion, conventional ready-made perfluoro compound dispersions may be supplied, or the dispersions may be prepared by blending the perfluoro compound and principal surfactant into water in any amounts and proportions which will provide uniform dispersions. Typical amounts are about 5 to 75% (w/v) of perfluoro compound, preferably 5 to 85% (w/v), and about 0.2 to 15%, preferably 1.0 to 15%, (w/v) of the surfactant, based on total volume of dispersion, i.e., 5 to 75 g. of perfluoro compound, and 1 to 15 g. of surfactant, per 100 ml. of total dispersion. Preferred amounts are about 5–25% (w/v) of the perfluoro compound and about 0.5–10% (w/v), preferably 2–10%, of the surfactant, more preferably 1.0–10.0% (w/v), on the same basis. However, the invention now permits, as standard practice, the preparation of dispersions in which the perfluoro compound is initially present in the range of about 25 to 60% (w/v), and the principal surfactant is initially present at about 10 to 20% (w/v), preferably about 5 to 10% (w/v).

The aqueous dispersions (both initially and finally) more usually comprise emulsions, preferably of the oil-in-water type but also including water-in-oil emulsions. In some cases the emulsions have a very fine particle size and appear transparent or solution-like to the unaided eye. The microemulsions which can be formulated with the dispersants of U.S. Pat. No. 3,828,085 have this characteristic and are preferred. Colloidal suspensions, while not excluded from use in this invention, are less preferred, particularly for systemic administration, because of their larger particle size range and lower stability.

The mixture of perfluoro compound, water and surfactant is dispersed by any conventional means of agitation, for example, by hand stirring, aeration, propeller agitation, turbine agitation, colloid milling, homogenizing, high-frequency or ultrasonic oscillation (sonication), and the like, including combinations of these techniques. In most instances emulsification is effective at ambient temperature. However, with some o the foregoing agitation means, excess heat may be generated during the formation of the emulsion and may be removed by known means, e.g., cooling jacket. The amount of mechanical energy input from the various agitation means can vary substantially depending on, for example, the amount of material being worked and the equipment used. Preferably, a coarse emulsion is first prepared with mild agitation, as in a Waring Blendor. The emulsion is then transferred to a homogenizer for completion of the emulsification and formation of the initial dispersion.

In the second step of preparing the dispersions of the invention, the perfluoro compound phase of the dispersion is concentrated to form a first phase comprising concentrated perfluoro compound-containing particles with the complexed surfactant, and a second, aqueous phase. One method of concentration is high speed centrifugation, for example at about 10,000 to 20,000 rpm, for about 0.5 to 3 hours. The selection of speed and the duration of centrifugation will depend on the type and proportion of perfluoro compound in the dispersion (the less dense or the less the amount of perfluoro compound, the greater the speed). In some batch centrifugations the result is a clear, supernatant liquid layer which rises to the top and a perfluoro compound-containing layer which falls to the bottom of the vessel. Cross flow filtration (described below) also provides a commercially proven technique which can be adapted to continuous concentration of the perfluoro compound phase.

In the light of the present specification, a person skilled in the art can select conditions which will produce the desired concentration of the perfluoro compound phase. Preferably, the concentration will be such that at least about 50% by weight of the surfactant originally in the dispersion is removed into the aqueous phase. Preferably not more than about 90% to 95% by weight of the surfactant is removed. The limits of the extent of surfactant removed will depend on the characteristics of the particular dispersion involved in a given instance, but can be determined by a person skilled in the art in the light of the present specification. In any event, the degree of concentration is not so great as to break the dispersion or to adversely affect the ability of the concentrated emulsion to be redispersed in added water in the third step of the process of the invention.

In the third step of the process, the two phases are physically separated, by decanting or similar means, thus removing the concentrated perfluoro compound phase from the aqueous phase containing free surfactant.

The foregoing description of the second and third steps is a sequential concentration and separation process. These steps may also be effected simultaneously by microfiltration (also known as "ultrafiltration"). Dispersions of this invention have particle sizes in the range of from about 0.05 to about 10 microns and therefore microfiltration may be a practical method of simultaneously concentrating the emulsion to form the concentrated perfluoro compound phase and separating such phase from the aqueous phase. Suitable microfiltration membranes include products available from the Millipore Company and Amicon Corporation as described, for example, in U.S. Pat. Nos. 3,615,024 and 3,856,569. In microfiltration, the dispersion is supplied to one side of a membrane and a pressure differential is applied across the membrane, so that a portion of the dispersion (the aqueous phase) passes through the membrane. The portion remaining on the supply side of the membrane is the perfluoro compound phase. Pressure or vacuum filtering or decantation can be used in conjunction with microfiltration, if desired. Pressure filtration is preferred over vacuum filtration due to a tendency to foaming during vacuum filtration.

In the last step of preparing the dispersions of the invention, the separated, concentrated perfluoro compound phase material, comprising perfluoro compound particles containing a small, residual amount of surfactant complexed therewith, is agitated in an aqueous medium (such as distilled or sterilized water) to redisperse the material. As described above, a second concentration and redispersion may also be carried out, in which case the first redispersion constitutes, in effect, a washing of the concentrated perfluoro compound phase. Conventional agitation or mixing means and conditions are employed. The amount of perfluoro compound in the final dispersion preferably will be about 20–75% (w/v) and the amount of principal surfactant preferably will be about 0.1–10.0% (w/v), preferably about 0.1–3.0% (w/v). The final dispersions intended for internal therapeutic use typically will have an average particle size of from about 0.05 to about 0.6 micron, and preferably will maintain an average particle size of less than 0.3 micron (e.g., 0.1 to 0.28 microns) for long periods, of the order of 35 weeks or more, at room temperature, thus indicating good stability.

Cross-flow filtration can be used to continuously reduce the concentration of undesired surfactant in the aqueous phase of an initial dispersion and to form a final dispersion having a desired concentration of perfluoro compound material. In this method, an aqueous medium (not containing the surfactant it is desired to remove) is added intermittently or continuously to a filtration vessel charged with initial perfluoro compound dispersion. As the filtration proceeds with concentration and separation of the perfluoro compound phase of the dispersion, the aqueous medium which is added replaces or "washes out" the aqueous phase of the initial dispersion. This results in controlled dilution of the aqueous phase of the initial dispersion, such that water containing undesired surfactant is removed and the concentration of undesired surfactant in the remaining aqueous phase is substantially reduced or eliminated. Also, a desired concentration of perfluoro compound phase material is obtained.

Where necessary, additional non-toxic ("auxiliary") surfactant (either the original surfactant, or lecithin or yolk phospholipid) may be added to the aqueous medium prior to the redispersion or may be added during or after the redispersion to further promote the redispersion. Small amounts sufficient to aid redispersal may be useful where needed as long was these amounts do not adversely affect the improved properties of the redispersed material. From about 0.1 to about 5% (w/v) of such surfactant may be useful. Other agents may be added as desired during the redispersion in place of or in addition to the auxiliary surfactant, such as coupling agents, cryogenic agents and the like. The resultant dispersion may be milky or transparent, depending on the perfluoro compound, surfactants and proportions, and the other additives.

The foregoing process for preparing dispersions according to the invention can be modified to collect, screen or classify the particles comprising the concentrated, perfluoro compound phase in order to assist in obtaining a desired particle size range in the final dispersion. Commercial centrifugation systems developed for recovery and concentration of antibiotics, protein molecules or viruses, for example, are readily adaptable to separation and/or classification of the perfluoro compound containing particles of the invention and to removal of uncomplexed surfactant. The high density of the particles as compared to the aqueous phase of the dispersions makes such systems well suited to practice of the invention. Moreover, the separation or classification may be practiced batch-wise or continuously, depending on the type of centrifugation apparatus.

For example, the De Laval countercurrent separator comprising a cylinder spinning on its vertical axis and having apertures radially spaced-apart on a horizontal cover plate on the upper end, may receive initial dispersion through the lower end. The dispersion will rise in the cylinder over the interior wall and the particles are then classified through the apertures of the plate into a plurality of streams such that desired, fine particles can be segregated from undesired, coarse particles. Simultaneously, aqueous medium containing uncomplexed surfactant is withdrawn. Further classification can be practiced on any of the streams or any of the streams can be sent to a redispersion station for preparation of the final dispersion.

A tubular bowl centrifuge permits not only classification in the manner of the cylindrical centrifuge described above but also will permit continuous concentration of the perfluoro compound phase, separation and redispersion. In this system, the initial dispersion is admitted near the lowest point of a rotating bowl. The perfluoro compound phase then separates from the aqueous phase and divides into several zones over the interior wall of the bowl according to particle size. Perfluoro compound Particles of desired sizes containing complexed surfactant may then be harvested and sent to redispersion while off-size particles may be discarded or recycled for repeat of initial dispersion. The aqueous phase containing free surfactant separated from the initial dispersion may be discarded, recovered or recycled for initial dispersion of perfluoro compound.

It is also practical by application of other known systems to avoid a total separation of the perfluoro compound phase from the aqueous phase of the initial dispersion, and to continuously form the final dispersion. One such technique is countercurrent centrifugal chromatography. In this process, the initial dispersion is continuously concentrated and classified according to desired particle size ranges, while aqueous medium containing free principal surfactant is drawn off, and aqueous medium (with or without an auxiliary surfactant) is added for the redispersion.

The foregoing and other techniques for practicing the process of the invention in a batch, continuous or semi-continuous manner are described in the technical literature such as in *Handbook of Separation Techniques for Chemical Engineers,* Schweitzer, P. A., Ed., McGraw-Hill Book Co., New York, 1975, specifically Section 4.5 entitled "Centrifugation."

When finally formulating the dispersions of the invention for systemic administration, it is desirable to add electrolytes and other materials to render the dispersions physiologically acceptable (such as isotonic with mammalian cells), and to adjust the pH, as necessary. A suitable pH range is 7.2–7.4. Among the additives conventionally used to render fluids physiologically acceptable are buffers such as sodium bicarbonate and mixtures such as Ringer's Solution. Other materials conventionally employed in pharmaceutical preparations and known to the skilled formulator may also be added to the dispersions. These include viscosity modifiers, stabilizers (against degradation due to freezing or contamination, for example), cryogenic preservatives, diluents, encoding agents, and the like. Among such additives may be mentioned glycerin, dimethylsulfoxide, various gelatins both natural and synthetic, and polyols such as sorbitol.

In using dispersions of the invention for drug delivery, the drug, if sufficiently lipophilic may be admixed with the perfluoro compound in desired proportions. This mixture can then be used to form the initial perfluoro compound dispersion, which is then processed to the final perfluoro compound dispersion in accordance with the method of the invention. Alternatively, the drug may be added in a desired amount to the concentrated perfluoro compound phase resulting from the concentration and separation steps of the invention, followed by the redispersion step to form a final dispersion containing the drug. As a third approach, the drug may be added to the final perfluoro compound dispersion in the requisite amount. The lipophilicity of the drug relative to the perfluoro compound material is an important consideration for selection of drugs for effective delivery, the more lipophilic the drug, the more successful will be the delivery, as described in the aforementioned U.S. application Ser. No. 580,760.

The invention is further described and illustrated in the following examples.

EXAMPLE 1

An initial emulsion was prepared in a conventional manner (U.S. Pat. No. 4,105,798) by dissolving Pluronic F-68 polyoxyethylenepolyoxypropylene copolymer surfactant (molecular weight about 8200) in distilled water to a concentration of 4.375% (w/v) and then adding to the solution to a concentration of 25% (w/v) a purified perfluorocarbon (perfluoro compound) consisting of a liquid mixture (about 80/20 by weight) of F-1,3-dimethyladamantane and F-trimethylbicyclo [3.3.1] nonane. The resulting composition is first admixed in a Waring Blendor to form a crude dispersion which is then transferred to a Mantin-Gaulin homogenizer and admixed to form a stable, uniform, clear emulsion.

Equal amounts of the emulsion were added to the first and second tubes of a two tube laboratory centrifuge and spun for 30 minutes at 12,500 RPM and relative centrifugal force maximum g's of 20,000 to concentrate the perfluoro compound phase. Each sample separated into a top supernatant phase and a bottom gelatinous perfluoro compound phase of which, in the first tube, 28.7 g. was supernatant and 15.4 g. was gel and, in the second tube, 28.5 g. was supernatant and 15.5 g. was gel. The two phases of each tube were separated by decanting and both supernatants were found to have a density of 1.0148, indicating that of the original 25% perfluoro compound, 23.9% was in the gel and only 1.1% was in the supernatant. The gel from the second tube was shaken with 41 ml. of distilled water and was found to disperse well to a substantially transparent emulsion containing 20% (w/v) of the perfluoro compound (by GC analysis). Particle size analysis with laser spectroscopy indicated a mean average particle size of 0.17 micron. The emulsion remained clear and stable after 104 days storage at 5° C. (average). At the end of that time, the average particle size was 0.24 micron.

Since the bulk of the initially formed emulsion upon centrifugation and separation was a liquid material which was not used for the redispersion, most of the original surfactant was not present in the redispersed emulsion; however, a small but sufficient amount had remained with the perfluoro compound phase to enable the perfluoro compound material to redisperse when shaken with the distilled water. Accordingly, the final dispersion contained a greatly reduced amount of the surfactant as compared with the amount present in the original emulsion, but essentially all of the surfactant in the final emulsion remained complexed with the perfluoro compound particles and only a minute amount, if any, transferred into the continuous phase.

EXAMPLE 2

In another experiment, conducted essentially as described in Example 1, an initial, conventionally prepared, stable and uniform emulsion containing 25% (w/v) of the same perfluoro compound, 4.375% (w/v) of the same surfactant and 1.25% (w/v) of glycerin (as a cryogenic agent) was found to have a viscosity of 2.5 centipoise at room temperature and a mean average particle size of 0.11 micron with less than 1% of the particles exceeding 0.3 micron. The emulsion was centrifuged at 3500 RPM for 6.1 hours at 3100 relative centrifugal force maximum g's (force of gravity) whereupon the two phases separated into a supernatant top layer and a gelatinous perfluoro compound bottom layer. The gel was separated from the supernatant and portions of the gel were redispersed in amounts of distilled water sufficient to provide two final emulsions, an emulsion A containing 25% (w/v) of the perfluoro compound and 1.9% (w/v) of the surfactant, and an emulsion B containing 50% (w/v) of the perfluoro compound and 3.4% (w/v) of the surfactant.

The reduced amount of surfactant in the final emulsions relative to perfluoro compound concentration indicated that the bulk of the surfactant present in the initially formed dispersion had been removed with the supernatants. The final emulsions were clear, uniform and stable. Emulsion A had a viscosity of 1.3 centistokes. Emulsion B had a viscosity of 3.1 centistokes. From a plot of viscosity versus perfluoro compound concentration of the initial and final emulsions it was determined that an emulsion prepared in accordance with the invention could contain up to about 42.7% (w/v) of the perfluoro compound without an increase in viscosity as compared with the initial emulsion. This example thus demonstrates the ability, in accordance with the invention, to substantially reduce the concentration of surfactant while providing, at an acceptable viscosity, a higher concentration of perfluoro compound than was heretofore deemed possible, without diminishing the uniformity, clarity and stability of the emulsion.

EXAMPLE 3

A series of experiments was conducted to study particle size, viscosity and stability of reconstituted emulsions prepared in accordance with the invention relative to perfluoro compound and surfactant concentrations as compared with conventionally prepared emulsions. The perfluoro compound and surfactant components were the same as in Example 2. Any differences in concentrations of the components and test conditions are shown in Table I below together with the test results wherein "PFC" means perfluoro compound. Runs 1, and 4 and 5 comprise the initial and final dispersions, respectively, of Example 2. Run 10 is the experiment of Example 1. Runs 1-3 are controls, i.e., initial, conventionally prepared, stable emulsions which were not centrifuged as were the emulsions used to prepare the reconstituted emulsions of runs 4-10. The reconstituted emulsions of runs 4-9 were prepared as described in Example 2, i.e., by centrifuging samples of the control emulsion of run 1, separating the resulting gel and supernatant layers, and redispersing the gels in amounts of distilled water sufficient to provide the indicated perfluoro compound concentrations. The surfactant concentrations were calculated as differences between the initially known concentrations and concentrations in the separated supernatant solutions. Initial surfactant concentrations and perfluoro compound concentrations were determined by density and chromatographic analysis for the perfluoro compounds.

The results show that stable, low viscosity emulsions can be effectively prepared in accordance with the invention to contain substantially greater concentrations of perfluoro compound and lower concentrations of surfactant than were achievable in the past. Consequently, the emulsions will have greater capacity for gas transfer but with reduced toxicity due to surfactant, and therefore, will provide substantially improved therapeutic benefits.

TABLE I

| RUNS | Gel Refrigeration, Days (5° C., avg.) | Emulsion Refrigeration, Days (5° C., avg.) | Centrifuge Speed, RPM | Centrifuge Time, hrs. | Concentrations, % (w/v) | | | Supernatant Density, g/cc | Dispersion Viscosity CPS | Particle Size. Vol. Avg., micron |
|---|---|---|---|---|---|---|---|---|---|---|
| | | | | | PFC | Glycerin | Surfactant | | | |
| Controls | | | | | | | | | | |
| 1 | — | 0 | — | — | 25 | 1.25 | 4.375 | 1.1289 | 2.5 | 0.11 |
| 2 | — | 1 | — | — | 25 | 1.25 | 4.375 | 1.1289 | 2.5 | 0.11 |
| 3 | — | 8 | — | — | 25 | 1.25 | 4.375 | 1.1289 | | 0.135 |
| 4 | 7 | 1 | 3500 | 6.1 | 25 | 0.24 | 1.9 | 1.1249 | 1.3 | 0.145 |
| 5 | 7 | 1 | 3500 | 6.1 | 50 | 0.48 | 3.4 | 1.2520 | 3.1 | 0.147 |
| 6 | 7 | 8 | 3500 | 6.1 | 25 | 0.24 | 1.9 | 1.1249 | | 0.185 |
| 7 | 7 | 8 | 3500 | 6.1 | 50 | 0.48 | 3.4 | 1.2520 | | 0.260 |
| 8 | 21 | 1* | 3500 | 6.1 | 25 | | | | | 0.195 |
| 9 | 7 | 15 | 3500 | 6.1 | 25 | 0.24 | 1.9 | 1.1249 | | 0.185 |
| 10 | 1 | 104 | 12,500** | 0.5 | 25 | | | 1.0148 | | 0.240 |

*Not refrigerated - maintained at room temperature.
**Lourdes Angle Head Tabletop centrifuge operating at 20,000 relative centrifugal force (RCF) maximum g's.
All other centrifugations were with a DPR 6000 Swinging Bucket Head centrifuge. International Equipment Company, operating at 3100 relative centrifugal force maximum g's.

EXAMPLES 4–13

An additional series of runs was carried out similar to those of Examples 1–3 in order to demonstrate the percent surfactant which remains complexed with the perfluorocarbon in the reconstituted emulsion. As shown in Table 2, varying amounts of different combinations of surfactants and perfluoro compounds were employed, principally Pluronic F-68 ("F-68"), XMO-10 (as defined below), or lecithin ("Lec") as the surfactants, and F-1,3-dimethyladamantane ("DMA") or F-methyladamantane ("MA") as the perfluoro compounds.

The initial emulsions for the various runs were prepared in the following manner:

F-68/DMA 90 g. of water was added to 10 g. of Pluronic F-68, and stirred to prepared an F-68 solution. Then 72 g. of perfluorocarbon was added and stirred vigorously again by a mixer to prepare a coarse mixture. The coarse emulsion was placed in a liquid reservoir of a microfluidizer and circulated while maintaining the liquid temperature at 40°±3° C. After the emulsification, sterile water was added to the homogenized product to obtain a final perfluorocarbon concentration of 25% w/v and F-68 concentration of 3.5% w/v.

Lec/MA

A 10% egg yolk phospholipid surfactant solution was made by adding 70 grams of egg yolk phospholipid to a volume of 700 ml with water. This was prepared with an ULTRAMIX for approximately 2 minutes at a 70 speed setting. 1000 gm of perfluoromethyladamantane was added to the 10% egg yolk phospholipid solution and the mixture dispersed with an ULTRAMIX for approximately 2 minutes at a 70 speed setting. The dispersion was charged to a Gaulin homogenizer with a 10,000 psi first stage setting and a 1,000 psi second stage setting, with temperature maintained at 55° to 60° C. Fifteen passes of the material were made under these conditions. 2800 ml of water were added to the resulting partially emulsified dispersion, and the diluted dispersion subjected to five more passes through the homogenizer under the same conditions. This procedure yielded a final emulsion of 25% (w/v) of perfluoromethyladamantane and 1.75% (w/v) of egg yolk phospholipid.

Lec/DMA

A 10% egg yolk phospholipid surfactant solution was made by adding 70 gram of egg yolk phospholipid to a volume of 700 ml with water. This was prepared with an ULTRAMIX for approximately 2 minutes at a 70 speed setting. 1000 gm of perfluorodimethyladamantane was added to the 10% egg yolk phospholipid solution and the mixture dispersed with an ULTRAMIX for approximately 2-3 minutes at a 70 speed setting. The dispersion is charged to a Gaulin homogenizer with a 10,000 psi first stage setting and a 1,000 psi second stage setting, with temperature maintained at 55° to 60° C. Ten passes of the material were made under these conditions. 2800 ml of water were added to the resulting partially emulsified dispersion, and the diluted dispersion subjected to five more passes through the homogenizer under the same conditions. This procedure yields a final emulsion of 25% (w/v) of perfluorodimethyladamantane and 1.75% (w/v) of egg yolk phospholipid.

Following preparation of the initial emulsions, the percent of surfactant present complexed with the perfluorocarbon in the whole and redispersed emulsions was determined in accordance with the following general procedures:

1. A 5 ml sample of the initial emulsion was pipetted into a tared aluminum weighing dish and placed in an oven at 100° C. for 5–8 hours in order to drive off the perfluoro compound and water. The residue, comprising surfactant, was then weighed. The dried sample was returned to the oven to dry for an additional hour. (A weight loss of less than 1% of the previous net loss indicates that the sample should be considered dry. Supernatant and wash solutions require 2–6 hours to dry, while whole emulsions and reconstituted gels require 6–10 hours to dry.) This residue represents the amount of surfactant in the total emulsion.

2. A second sample, (7 ml) of the initial emulsion was then pipetted into a stoppered Fisher polycarbonate centrifuge tube, and spun down at 15,000 rpm at 4° C. in a Beckman Angle Head Rotor for 30 minutes in order to form a supernatant phase and a gelatinous perfluoro compound phase (gel). No perfluorocarbon remained in the supernatant or in subsequent centrifuged wash solutions under these conditions.

3. The supernatant was then transferred to an aluminum weighing dish, dried, and the total remaining solids i.e. non-complexed surfactant, was determined. The drying was carried out at 100° C., for about 3 hours to remove all water. Measurement of the amount of surfactant complexed with the gel was by difference.

4. The gel recovered from Step 3 was then resuspended in 7 ml of distilled water by redispersing in a Vortex mixer for 5 minutes, thus forming an emulsion of this invention. The emulsion was then centrifuged as in Step 2 in order to again separate gel from the supernatant. The total solids (non-complexed surfactant) in this supernatant were measured as in Step 3; this first redispersion also constituted a first washing of the gel to remove non-complexed surfactant, and to determine the amount of non-complexed surfactant in the supernatant. (Optionally, a second washing and centrifuging of the gel may be performed as in Step 3, together with measurement of the solids recorded from this second supernatant (non-complexed surfactant), as above.)

5. The gel from Step 4, which constitutes an example of the perfluoro compound phase of this invention, was recovered for determination of the amount of bound surfactant by resuspending it with 5 ml of distilled water with the aid of a Vortex mixer. This suspension was transferred to a tared aluminum dish, together with two 1 ml washes of the tube. This gel was then dried in an oven for at least 6 hours or until constant weight was achieved. Under these conditions, the volatile perfluorocarbon is driven off; the residue after this drying represents the complexed surfactant of the emulsion of this invention, whereas the free surfactant of the emulsion in the supernatant was measured in Step 4.

Following the above procedures, the amounts of surfactant in the whole emulsion, as well as those amounts of surfactant recovered from each of the supernatants, were measured along with the weights of the gels of each emulsion and the surfactants bound to the gels of each emulsion. From these measurements the Percentages i.e. proportions, of complexed surfactant in the whole emulsion, and the percentages of surfactant complexed with the gel of the redispersed emulsions were calculated and reported in Table 2 below for two or more runs each of four different combinations of surfactants and perfluoro compounds. (Included in this table (as Example 11) are the results of comparative Example 14, below, as well as comparative Examples 12 and 13.)

From these data it will be seen that in every case the percentage of complexed surfactant, relative to the total amount of surfactant in each emulsion, was increased by approximately 30 to 50% in the redispersed emulsions of this invention as compared to the amounts in the whole emulsions previously employed in the art. In Example 4, for instance, the proportion of complexed surfactant is 31.5% in the initial dispersion, whereas the comparable proportion for the redispersed emulsion of this invention is 76.9%.

Conversely, this signifies a marked decrease of free surfactant in the supernatant of the redispersed emulsion compared to those amounts found in the whole emulsions of the prior art, which free surfactant has caused problems of toxicity and the like.

solutions were decanted away from the gels into tared weighing dishes and taken to constant weight.

It was found the 40.4 wt. % of the XMO-10 remained in the supernatant solution, and that 59.6% (by difference) of the XMO-10 was bound to the fluorocarbon emulsion particle.

Thus, it will be seen that the prior art composition of surfactant and perfluorocarbon contains at most about 60% by weight complexation of the surfactant present compared with the approximately 75–99% of the compositions of this invention.

In addition, using the above emulsion, two additional measurements were made in accordance with the procedures used for Examples 4–13 to determine the amount of surfactant bound to the DMA of this initial emulsion. As contrasted with the 59.6 wt. % reported above, using this other procedure measurements of 51.2 and 50.3% respectively were obtained, as reported in Examples 12 and 13 above, thus giving an average of about 55% by weight.

TABLE 2

| EXAMPLE | SURF/PFC | % (w/v) PFC$^{(d)}$ | % (w/v) SURF$^{(e)}$ | WEIGHT PERCENTAGE OF SURF$^{(f)}$ WHOLE EMUL. | WEIGHT PERCENTAGE OF SURF$^{(g)}$ REDISP. EMUL. |
|---|---|---|---|---|---|
| 4 | F-68/DMA | 25 | 3.15 | 31.5 | 76.9 |
| 5 | F-68/DMA | 25 | 3.26 | 30.2 | 74.3 |
| 6 | LEC$^{(a)}$/MA | 25 | 1.67 | 43.2 | 93.6 |
| 7 | LEC$^{(a)}$/MA | 25 | 1.66 | 43.2 | 94.8 |
| 8 | LEC$^{(a)}$/DMA | 25 | 1.76 | 54.3 | 99.2 |
| 9 | LEC$^{(a)}$/DMA | 25 | 1.79 | 54.5 | 99.2 |
| 10 | LEC$^{(a)}$/DMA | 25 | 1.87 | 50.6 | 98.9 |
| 11 | XMO-10/DMA$^{(b)}$ | 20 | 2.0 | 59.6 | N.A. |
| 12 | XMO-10/DMA$^{(c)}$ | 20 | 2.0 | 51.2 | 85.3 |
| 13 | XMO-10/DMA$^{(c)}$ | 20 | 2.0 | 50.3 | 84.8 |

$^{(a)}$The lecithin used was egg yolk phospholipid (available from Kabi Vitrum, Inc., Stockholm, Sweden).
$^{(b)}$Prepared and measured as described in Example 14, below.
$^{(c)}$Prepared as described in Example 14, below; measurements were made in accordance with the procedures employed for runs 4–10.
$^{(d)}$% (w/v) perfluoro compound of the initial (whole) emulsion.
$^{(e)}$% (w/v) of surfactant of the initial (whole) emulsion.
$^{(f)}$Percentage of surfactant complexed with the gel of the initial emulsion relative to the total amount of surfactant in the supernatent and gel of the initial emulsion.
$^{(g)}$Percentage of surfactant complexed with the gel of the redispersed emulsion relative to the total amount of surfactant in the redispersed emulsion of this invention.

In addition to the above measurements, each of the above emulsions was subjected to a second spinning down and redispersion, i.e., a second "washing". In each case except for the XMO-10 surfactant the percentages remained the same or increased slightly; the XMO-10 emulsion percentage for complexed surfactant decreased, signifying that the emulsion was not as stable as the others tested.

EXAMPLE 14

For comparison, as reported in Example 11 above, Example 1 of U.S. Pat. No. 4,461,717 was repeated as follows, employing as the surfactant an amidoamine oxide ("XMO-10") of that patent, having the formula:

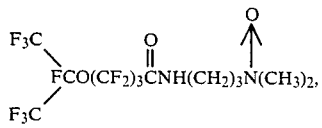

and as the perfluorocarbon, a mixture of F-dimethyladamantane (DMA) and F-trimethylbicycloxonane:

An emulsion consisting of 20 wt. % w/v F-DMA and 2 wt. % w/v XMO-10 was placed in four (4) tared centrifuge tubes. Each of the tubes was centrifuged at 15,000 rpm's (32,000 g's) for 1 hour. The supernatant

What I claim is:

1. A composition comprising a stable, uniform, aqueous dispersion of a perfluoro compound having gas transfer properties and a surfactant, wherein greater than about 75% by weight of the surfactant present in said dispersion is complexed with the perfluoro compound.

2. The composition of claim 1 wherein at least 85–90% by weight of the surfactant present is complexed with the perfluoro compound.

3. The composition of claim 1 wherein the perfluoro compound is a non-aromatizable perfluorinated $C_9$–$C_{18}$ polycyclic hydrocarbon containing at least two bridgehead carbon atoms linked through a bridge containing at least one carbon atom, and the surfactant is nonionic.

4. The composition of claim 3 wherein the composition comprises a mixture of F-dimethyladamantane and F-trimethylbicyclo[3.3.1]nonane.

5. The composition of claim 1 or 3 wherein the surfactant is a fluorinated amidoamine oxide compound.

6. The composition of claim 1 or 3 wherein the surfactant is an oxyethylene or oxypropylene homopolymer, or block copolymer of ethylene oxide and propylene oxide.

7. The composition of claim 1 or 3 wherein the surfactant is a phospholipid selected from the group consisting of lecithin and yolk phospholipid.

8. The composition of claim 1 wherein the dispersion contains additional surfactant.

9. A process for preparing an aqueous dispersion of a perfluoro compound having gas transfer properties, which comprises:
  (a) providing an initial dispersion comprising (i) a perfluoro compound phase containing a surfactant complexed with the perfluoro compound, and (ii) an aqueous phase containing uncomplexed surfactant;
  (b) concentrating the perfluoro compound phase;
  (c) recovering the concentrated perfluoro compound phase from the aqueous phase; and
  (d) redispersing the concentrated perfluoro compound phase with an amount of an aqueous medium effective to redisperse the perfluoro compound phase and thereby to form a final dispersion.

10. The process of claim 9 wherein additional surfactant is added in step (d) in an amount effective to promote redispersion of the concentrated perfluoro compound phase.

11. Process of claim 9 wherein greater than about 65% by weight of the surfactant present in the final dispersion is complexed with the perfluoro compound.

12. The process of claim 9 wherein the concentrating of step (b) is effected by centrifugation.

13. The process of claim 9 wherein the initial dispersion is prepared by agitating a mixture of perfluoro compound and a surfactant in an aqueous medium.

14. The process of claim 9 wherein particles having a desired average particle size of from about 0.05 to 0.6 micron are recovered from the perfluoro compound phase recovered in step (c) and redispersed in step (d), and the remaining undesired particles falling outside said desired range are thereafter recovered.

15. The process of claim 9 wherein particles having a desired average particle size from about 0.05 to 0.6 micron are recovered from the perfluoro compound phase recovered in step (c) and redispersed in step (d), the remaining undesired particles falling outside said desired range are thereafter recovered and recycled to the initial dispersion of step (a).

16. The process of claim 9 wherein the perfluoro compound is a non-aromatizable perfluorinated $C_9$–$C_{18}$ polycyclic hydrocarbon containing at least two bridgehead carbon atoms linked through a bridge containing at least one carbon atom, and the surfactant is nonionic.

17. The process of claim 16 wherein the perfluoro compound comprises a mixture of F-dimethyladamantine and F-trimethylbicyclo[3.3.1]nonane.

18. The process of claim 9 wherein at least 75% by weight of the surfactant present in the final dispersion is complexed with the perfluoro compound.

19. The process of claim 9 wherein at least 85–90% by weight of the surfactant present in the final dispersion is complexed with the perfluoro compound.

20. The aqueous dispersion produced by the process of claims 9, 11, 16 or 17.

* * * * *